(12) United States Patent
Cruijsberg et al.

(10) Patent No.: US 7,339,087 B2
(45) Date of Patent: Mar. 4, 2008

(54) PYROLYSIS

(75) Inventors: Emil Eduard Antonius Cruijsberg, Amsterdam (NL); Jeroen Cornelis Josephus Maria Goossens, Amsterdam (NL); Jeroen Van Westrenen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 592 days.

(21) Appl. No.: 10/095,284

(22) Filed: Mar. 11, 2002

(65) Prior Publication Data
US 2002/0134018 A1 Sep. 26, 2002

(30) Foreign Application Priority Data
Mar. 15, 2001 (EP) .................... 01302420

(51) Int. Cl.
*C07C 4/04* (2006.01)
*C10G 9/00* (2006.01)

(52) U.S. Cl. ............. 585/648; 585/652; 208/130; 208/128

(58) Field of Classification Search ............. 585/64–8, 585/652; 208/130, 128
See application file for complete search history.

(56) References Cited

U.S. PATENT DOCUMENTS 5,567,305 A * 10/1996 Jo .................... 208/48 R

FOREIGN PATENT DOCUMENTS

DE 3708332 A1 9/1988

* cited by examiner

Primary Examiner—Thuan Dinh Dang

(57) ABSTRACT

Process for pyrolyzing a light feed in a pyrolysis furnace designed for pyrolyzing heavy feed, in which process part of the light feed is introduced at the feed inlet of the convection zone of the pyrolysis furnace and further light feed is introduced into the convection zone together with the dilution gas.

14 Claims, 1 Drawing Sheet

PYROLYSIS

The invention pertains to a process for pyrolyzing a light feed.

BACKGROUND OF THE INVENTION

The production of olefins, in particular ethene, is in general achieved by pyrolyzing petroleum hydrocarbon feedstocks such as gas oil obtained from an atmospheric distillation column, naphtha, natural gas liquids, butane, propane or ethane. Some crackers can use even heavier feedstocks, such as gas oil obtained from a vacuum distillation column.

Pyrolysis is also called steam cracking and comprises thermal cracking of hydrocarbons in the presence of dilution gas. The process comprises a convection zone, a cracking zone, a cooling zone and a separation zone. The pyrolysis furnace comprises the convection zone and the cracking zone. The convection zone comprises a first preheating zone and a second preheating zone. Generally, feed is heated in the first preheating zone, and dilution gas is added to the feed before the mixture of feed and dilution gas is sent to the second preheating zone. If the feed is liquid, generally at least part of the feed is vapourized in the first preheating zone.

It is well known that coke deposits in the cracking zone during operation. This coke layer inhibits heat transfer from the heating means in the cracking zone, it raises the wall temperature and it reduces the cross-sectional flow area of the tube. Because of the coke formation in the cracking zone, the pyrolysis furnace must be regularly shut down to remove the coke.

Generally, an olefin plant for converting liquid feeds will contain several pyrolysis furnaces of which the majority is designed for pyrolyzing liquid feed and generally a single furnace is designed for pyrolizing gaseous feed. The majority of the gaseous feed is usually produced in the olefin plant itself. If a pyrolysis furnace designed for gaseous feed is taken out of service, the feed needs to be processed in another pyrolysis unit. As there is generally not sufficient spare capacity for pyrolyzing gaseous feed, the gaseous feed generally is sent to a pyrolysis unit designed for pyrolyzing liquid feed. However, only a relatively small amount of gaseous feed can be sent to a furnace designed for liquid feed. The narrower, longer tubes in the convection zone designed for liquid feed, cause a larger pressure drop. Therefore, in some instances, part of the gaseous feed is added to fuel gas when a pyrolysis furnace designed for gaseous feed is out of operation. Further, it is disadvantageous to process gaseous and liquid pyrolysis feed in a single pyrolysis furnace as the process conditions for the feeds differ.

Liquid feeds which can be subjected to pyrolysis comprise gas oil and naphtha. A gas oil generally has a higher initial and final boiling point than naphtha. Furnaces designed for treating a heavy feed will have a larger heat transfer surface area in the first preheating zone than furnaces designed for light feed as a heavy feed has a higher initial boiling point than light feed and the main aim of the first preheating zone is vapourizing (part of) the feed and heating the feed. If a light feed such as naphtha is fed to a furnace designed for pyrolysis of gas oil, the naphtha will generally be fully vapourized when having passed part of the first preheating zone. If the amount of light feed sent to the pyrolysis furnace would be the same as the amount of heavy feed for which the furnace was designed, there would be an unacceptable large pressure drop over the first preheating zone as a large amount of gas would flow through the first preheating zone. Therefore, only a relatively small amount of light feed can be treated in a furnace designed for a heavy feed.

A furnace designed for treating gaseous feed will have a smaller heat transfer surface area in the first preheating zone than a furnace designed for liquid feed as a gaseous feed does not need to be vapourized.

SUMMARY OF THE INVENTION

The present invention relates to a process which makes it possible to pyrolize light feed in a furnace designed for pyrolyzing heavy feed, more specifically to pyrolize gaseous feed in a furnace designed for pyrolyzing liquid feed. Therefore, better use can be made of the light feed when the pyrolysis furnace designed for the light feed is out of operation.

A process for pyrolyzing a light feed in a pyrolysis furnace designed for pyrolyzing heavy feed comprising:
(1) heating the feed in a convection zone comprising a feed inlet,
(2) further heating the product of the convection zone in a cracking zone thereby producing lower boiling products,
(3) cooling the lower boiling products of the cracking zone thereby producing a cooled product, and
(4) separating the cooled product into desired end-products, wherein light feed is introduced at the feed inlet of the convection zone and further light feed is introduced into the convection zone together with dilution gas.

DETAILED DESCRIPTION OF THE INVENTION

Figure 1:
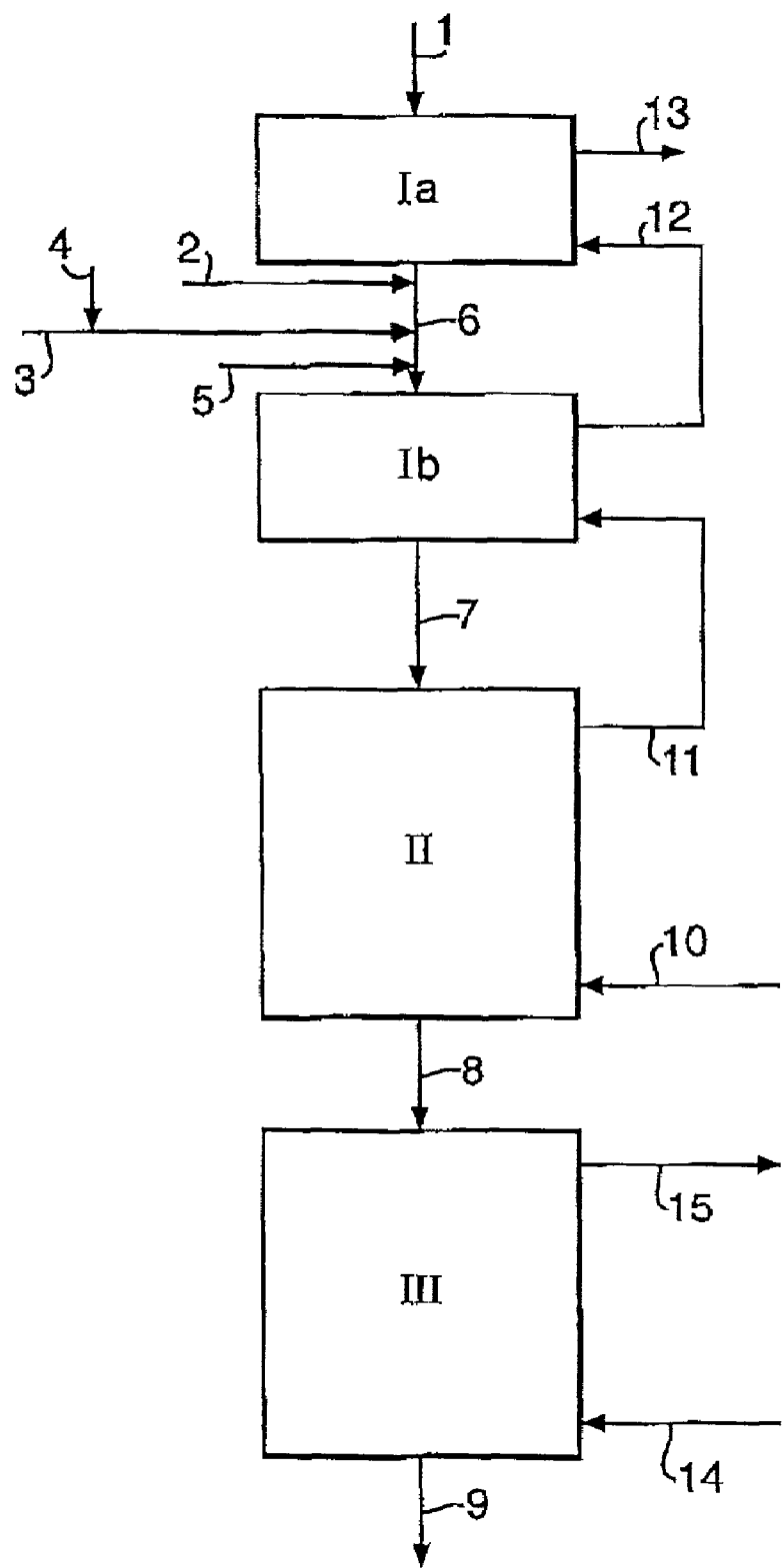
FIG. 1 is a preferred block flow diagram of the process.

It is to be understood that the scope of the invention may include any number and types of process steps between each described process step or between a described source and destination within a process step.

The light feed is pyrolyzed in a pyrolysis furnace designed for pyrolyzing heavy feed by a process comprising:
(1) heating the feed in a convection zone,
(2) further heating the product of the convection zone in a cracking zone where the feed is converted into lower boiling products,
(3) cooling the product of the cracking zone, and
(4) separating the cooled product into desired end-products, in which process light feed is introduced at the feed inlet of the convection zone and further light feed is introduced into the convection zone together with dilution gas.

Usually and preferably, all product of a process step will be subjected to the next process step. However, it is possible to send only part of the product of a process step to the next process step.

Feed can be introduced into the process at further inlets besides the standard inlet and the inlet where feed is introduced together with dilution gas. However, it is preferred to introduce feed only at the standard inlet of the convection zone and further feed together with dilution gas.

Dilution gas can be added at a single inlet, or can be added via several inlets. However, it is preferred to add dilution gas at a single inlet.

The temperatures mentioned in this specification are the temperatures which the feed attains.

Light feed differs from dilution gas in that light feed mainly consists of hydrocarbons containing at least 2 carbon atoms. Hydrocarbons consist of hydrogen and carbon, and optionally heteroatoms. Preferably, light feed contains at least 60% wt of hydrocarbons containing at least 2 carbon atoms, more specifically at least 70% wt, more specifically at least 80% wt, most specifically at least 90% wt.

A heavy feed is a feed having a higher initial boiling point than the light feed. Although the boiling range of a light and a heavy feed can overlap, the heavy feed will generally have both a higher initial boiling point and a higher final boiling point.

A gaseous feed is a feed of which the major part is gaseous upon entry into the convection zone, preferably at least 80% wt of the feed is gaseous, more preferably at least 95% wt is gaseous, most preferably the total feed is gaseous upon entry into the convection zone. Examples of feeds which are generally gaseous upon entry into the convection zone are ethane, propane, butane, and liquefied petroleum gas, or any combination of these feeds. Liquefied petroleum gas (LPG) is a mixture of light hydrocarbons, such as propane, isobutane and n-butane. Ethane can be obtained from wet natural gas and refinery waste gases. Ethane may be cracked alone or in combination with other compounds such as propane. Propane can be obtained from wet natural gases, natural gasolines and refinery waste gases. Butanes can be obtained from natural gasolines and refinery waste gases. Generally, LPG is obtained from natural gasolines and refinery gases. Preferably, the gaseous feed is ethane.

A liquid feed is a feed of which the major part is liquid upon entry into the convection zone, preferably at least 80% wt of the feed is liquid, more preferably at least 95% wt is liquid, most preferably the total feed is liquid upon entry into the convection zone. A liquid feed can be naphtha. The initial boiling point of naphtha can be from 0° C. to 100° C. while final boiling points can range from 90° C. to 250° C. Another liquid feed can be gas oil. The initial boiling point of gas oil can range from more than 100° C. to 300° C. while final boiling points can range from 300° C. to 600° C. Preferably, the furnace is designed for pyrolyzing naphtha or the furnace is designed for pyrolyzing gas oil. More preferably, the furnace is designed for pyrolyzing naphtha.

The convection zone of a pyrolysis process designed for a heavy feed differs from the convection zone designed for a light feed especially in the first preheating zone. The first preheating zone of a convection zone for a heavy feed will have a higher heat transfer surface area than the first preheating zone for a light feed. Although the precise heat transfer surface area depends on further circumstances such as process conditions applied and the hardware being used, someone skilled in the art will know from the heat transfer surface area of a first preheating zone in combination with the process conditions applied, for which feed the furnace has been designed.

The convection zone of a pyrolysis process designed for pyrolyzing liquid feed differs fundamentally from the convection zone of a gaseous feed pyrolysis process, especially in the first preheating zone. A convection zone for pyrolyzing liquid feed, more especially its first preheating zone, will have relatively narrow tubes while the feed will be in the convection zone, more especially the first preheating zone, for a longer time. The longer residence time in the convection zone can be attained by passing the feed more often through the convection zone, more especially the first preheating zone. The tubes present in a liquid feed convection zone will generally have a diameter of from 7 to 8 cm although different diameters can be used as well depending on the further conditions such as the length of the tubes, the number of passes, the acceptable pressure drop and the feed to be converted.

The convection zone, more especially the first preheating zone, for pyrolyzing gaseous feed will have wider tubes, while a relatively short residence time in the zone generally suffices for a gaseous feed. The short residence time is generally attained by passing the feed only a limited number of times through the zone. The tubes present in a gaseous feed convection zone will generally have a diameter of from 8 to 9 cm although different diameters can be used as well depending on the further conditions such as the length of the tubes, the number of passes and the acceptable pressure drop and the feed to be converted. The differences between a liquid feed convection zone and a gaseous feed convection zone are mainly due to the fact that gaseous feed does not need to be evaporated.

The convection zone generally comprises a first preheating zone and a second preheating zone between which is located an inlet for dilution gas. In the first preheating zone, the feed is heated. After the first preheating zone, dilution gas can be added to the feed and the mixture obtained can be heated further in the second preheating zone to a temperature just below the temperature at which cracking starts to occur. The temperature of the product obtained from the convection zone will usually be of from 400 to 800° C., depending upon the feed, more specifically of from 450 to 750° C.

The pyrolysis furnace may be any type of conventional olefins pyrolysis furnace designed for pyrolyzing heavy feed and operated for production of lower boiling products such as olefins, especially including a tubular steam cracking furnace. The tubes within the convection zone of the pyrolysis furnace may be arranged as a bank of tubes in parallel, or the tubes may be arranged for a single pass of the feedstock through the convection zone. Within each bank, the tubes may be arranged in a coil or serpentine type arrangement. At the inlet, the feed may be split among several tubes, or may be fed to one single pass tube through which all the feed flows from the inlet to the outlet of the first stage preheater.

Preferably, the first and/or second preheating zone of the convection zone comprise a multiple pass tubular reactor in which feed is passed through the first and/or the second preheating zone via more than one tube. Multiple pass tubular reactors often contain tubes having connections at their ends leading feed from the one tube to the next tube until the feed is sufficiently heated to be mixed with dilution gas and be passed to the second preheating zone, or to be sent to the cracking zone.

In the process according to the present invention, part of the light feed is introduced to the convection zone at the standard feed inlet where usually heavy feed is introduced.

To circumvent unacceptable throughput limitations, the further light feed which is introduced together with the dilution gas, can be introduced either separate from the dilution gas or can have been mixed with the dilution gas before being introduced into the process. Usually, the further light feed will be the remaining feed which can not be introduced via the standard inlet for the reasons discussed above. However, there might be reasons for not introducing all remaining light feed into the process of the present invention. If the light feed is introduced separate from the dilution gas, the feed can be introduced either before the introduction of the dilution gas or after the introduction of the dilution gas. Preferably, the points of introduction of the further light feed and the dilution gas will be close together. If the further light feed is introduced before introduction of the dilution gas, introduction too far apart would lead to an unacceptable pressure drop which is to be prevented in the process of the present invention.

The further light feed can be introduced after having been mixed with the dilution gas. However, if further light feed is introduced after having been mixed with dilution gas, more especially steam, the temperature of the mixture might decrease before introduction into the convection zone such that condensation starts by which water droplets are formed. The presence of water droplets should generally be avoided as these can cause erosion.

If the further light feed is introduced after introduction of the dilution gas, the introduction is preferably such that the further light feed is heated sufficiently for cracking in the subsequent cracking zone.

Although it is preferred to introduce the majority of the feed via the combination of the standard feed inlet and an inlet close to the inlet for the dilution gas, minor amounts of feed can be introduced at different locations.

Most preferably, the further light feed is introduced into the convection zone before dilution gas is introduced.

The pressure and temperature at which the feed is fed to the inlet of the first preheating zone is not critical, typically the temperature will be from about 0° C. to about 300° C.

The optimal temperature to which the feed is heated in the first preheating zone will depend upon the pressure of the feed, and the performance and operation of the remainder of the process. The product of the first preheating zone will generally have an exit temperature of at least 120° C. The upper range on the temperature of the feed in the first preheating zone is limited to the point at which the stability of the feed is impaired. At a certain temperature, the coking propensity of the feed increases. This temperature limit would apply to both the first and the second preheating zone and all tubes in these zones. Preferably, the exit temperature of the feed within the first preheating zone is not more than 520° C., and most preferably not more than 500° C.

The heating elements in the first and second preheating zone in the convection zone is typically a bank of tubes, wherein the contents in the tubes are heated primarily by convective heat transfer from the combustion gas exiting from the cracking zone of the pyrolysis furnace, so-called flue gas. However, different heating elements can be used as well.

The pressure within the first and second preheating zone is not particularly limited. The pressure is generally within a range of from 4 to 21 bar, more preferably of from 5 to 13 bar.

In the process of the present invention part of the light feed is introduced via the standard feed inlet of the convection zone, and part of the light feed is introduced further downstream in the convection zone. The weight ratio of light feed introduced at the standard feed inlet to light feed introduced together with dilution gas generally is of from 1:3 to 20:1, preferably of from 1:2 to 15:1, more preferably of from 1:1 to 5:1.

Dilution gas is added to the convection zone. This can be done at any point in the convection zone. Dilution gas is preferably added at a point external to the pyrolysis furnace for ease of maintaining and replacing equipment.

The dilution gas is a vapour at the injection point into the convection zone. Examples of dilution gases are steam, preferably superheated steam (steam above its boiling point), methane, ethane, nitrogen, hydrogen, natural gas, dry gas, refinery off gases, and a vapourized naphtha. Preferably, the dilution gas is superheated steam, a refinery off gas, or mixtures thereof. Most preferably, the dilution gas is superheated steam.

If the dilution gas is mixed with the further light feed before being introduced into the process, the temperature of the dilution gas before being mixed with the further light feed to be introduced into the process, is preferably so high that the combination of further light feed and dilution gas can be introduced in the process without condensation of any part of the dilution gas.

Typical dilution gas temperatures at the dilution gas/feed junction range of from 140° C. to 800° C., more preferably of from 150° C. to 780° C., more preferably of from 200 to 750° C.

The pressure of dilution gas is not particularly limited, but is preferably sufficient to allow injection. Typical dilution gas pressures added to the crude oil is generally within the range of from 6 to 15 bar.

It is desirable to add dilution gas between the first preheating zone and the second preheating zone in an amount which will generally be not more than 1 kg of dilution gas per kg of feed. However, there can be circumstances in which a higher amount of dilution gas can be advantageous.

The mixture of dilution gas and feed is fed to the second preheating zone where the mixture is heated further. Tubes of the second preheating zone can be heated by the flue gases from the cracking zone of the furnace. In the second preheating zone, the mix is fully preheated to near or just below a temperature at which substantial feedstock cracking and associated coke laydown in the preheater would occur.

Subsequently, the product of the convection zone is sent to the cracking zone. The temperature of the mixture of steam and feed is increased further under controlled residence time, temperature profile and partial pressure. The exit temperature of the product obtained in the cracking zone is generally of from 700 to up to 1000° C. more specifically of from 750 to 950° C. The pressure is generally within a range of from 2 to 25 bar, more preferably of from 3 to 18 bar.

The reactions in the cracking zone are highly endothermic, and therefore a high rate of energy input is needed.

On leaving the cracking zone, the products are generally immediately cooled. The temperature of the product will usually be reduced to a temperature of from 200 to 700° C., more specifically of from 250 to 650° C. to prevent degradation by secondary reactions. Cooling of the product obtained in the cracking zone can be done in any way suitable, such as by direct quenching or indirect quenching.

The cooled product is subsequently separated into the desired end-products. Separation of the desired end-products can start at cooling where heavy components can be removed. Further, during cooling the gas obtained can be compressed, and acids and water can be removed. Subsequently, the product can be dried and uncracked feed, ethane and propane may be recovered for recycling as pyrolysis feed. The cracking severity affects the composition of the product obtained.

Products of an olefins pyrolysis furnace include, but are not limited to, ethene, propene, butadiene, benzene, hydrogen, and methane, and other associated olefinic, paraffinic, and aromatic products. Ethene generally is the predominant product, typically ranging from 15 to 60% wt, based on the weight of the feed.

In a typical work-up, the product of the cracking zone is cooled with the help of a water quench, followed by multistage compression typically in 4 to 6 stages. Before the last compressor stage, the gas is treated with caustic to remove hydrogen sulphide and carbon dioxide. Acetylenes may be hydrogenated with hydrogen-rich compressor gas. After the last compression stage, the cracked gas is typically dehydrated by chilling and dried by use of molecular sieves. Methane and hydrogen can be removed in a demethanizer. In a demethanizer, the hydrocarbons containing 2 carbon atoms are produced overhead and the hydrocarbons containing 3 carbon atoms or more is a bottom product. The overhead stream can be hydrogenated to remove acetylene and then fractionated to produce ethene and ethane. The ethane can be recycled. The bottom product can be further fractionated, if appropriate, to remove heavy ends including compounds containing 4 carbon atoms or more. The overhead stream from a depropanizer can be hydrogenated to remove methylacetylene and propadiene, which can be recovered for sale or removed via other means. Propene can be obtained as overhead stream from the depropanizer, and the bottom propane fraction can be recycled.

As described above, the process of the present invention is especially advantageous if the light feed is a gaseous feed and if the heavy feed is a liquid feed. A light feed for which the present invention is especially advantageous is ethane.

The pyrolysis furnace for use in the present invention is advantageously a furnace designed for pyrolyzing naphtha or a furnace designed for pyrolyzing gas oil. Most frequently, the furnace will be a furnace designed for pyrolyzing naphtha.

A preferred process according to the present invention has been depicted in FIG. 1. However, the present invention is not limited to this preferred process.

Convection zone I consists of zone Ia, a first preheating zone and zone Ib, a second preheating zone. Zone II is a cracking zone and zone III is a cooling zone.

In this typical process, both the first and the second preheating zone are heated with the help of flue gas. Preferably, the flue gas is introduced into cracking zone II via line 10. Flue gas can have a temperature of up to 1350° C. After having been used in heating of cracking zone II, the flue gas is led via line 11 to the second preheating zone Ib. After having been used in heating the second preheating zone Ib, the flue gas can be sent to the first preheating zone via line 12. The flue gas can be removed from the first preheating zone via line 13.

Light feed to be subjected to the process of the present invention is introduced into the convection zone via line 1. The light feed is heated in preheating zone Ia. Dilution gas is added to the convection zone via line 3. Further light feed can be introduced into the process together with the dilution gas via line 2, 4 and/or 5.

By the term "together," the dilution gas and the further light feed can be introduced to the light feed, introduced into the convection zone via line 1, simultaneously or separately but close to each other. As discussed above, it is preferred to introduce the further light feed via line 2, close to but separate from the introduction of dilution gas. Another option is to mix at least part of the further light feed with dilution gas by adding light feed via line 4 to line 3. A further option is to introduce further light feed via line 5 which makes that further light feed is introduced after but close to introduction of the dilution gas. Via line 6, the light feed heated in the first preheating zone Ia is sent to the second preheating zone Ib.

The mixture of light feed and dilution gas is heated further in the second preheating zone Ib.

The heated mixture obtained is sent via line 7 to cracking zone II where the feed is converted into lower boiling products. The product of the cracking zone is sent via line 8 to zone III where the product is cooled. Cooling fluid can be introduced via line 14, and removed via line 15. The cooled product can be treated further in a separation zone (not shown) to obtain the desired products as described above.

We claim:

1. A process for pyrolyzing a light feed in a pyrolysis furnace designed for pyrolyzing heavy feed which process comprises:
   (1) heating the light feed in a convection zone, wherein the convection zone comprises:
      a feed inlet;
      a first preheating zone; and,
      a second preheating zone,
   (2) further heating the product of the convection zone in a cracking zone thereby producing lower boiling products,
   (3) cooling the lower boiling products of the cracking zone thereby producing a cooled product, and
   (4) separating the cooled product into end-products, wherein the light feed is introduced at the feed inlet of the convection zone and further light feed is introduced together with dilution gas between the first preheating zone and the second preheating zone.

2. The process of claim 1 wherein the light feed is a gaseous feed and the pyrolysis furnace is designed for liquid feed.

3. The process of claim 1 wherein the weight ratio of light feed introduced at the feed inlet to light feed introduced together with dilution gas is from 1:3 to 20:1.

4. The process of claim 2 wherein the weight ratio of light feed introduced at the feed inlet to light feed introduced together with dilution gas is from 1:3 to 20:1.

5. The process of claim 1 wherein the dilution gas is superheated steam.

6. The process of claim 1 wherein the light feed is ethane.

7. The process of claim 1 wherein the furnace is designed for pyrolyzing naphtha or the furnace is designed for pyrolyzing gas oil.

8. The process of claim 7 wherein the furnace is designed for pyrolyzing naphtha.

9. The process of claim 1 wherein further light feed is introduced into the convection zone before dilution gas is introduced.

10. The process of claim 2 wherein the further light feed is introduced into the convection zone before dilution gas is introduced.

11. The process of claim 3 wherein the dilution gas is superheated steam.

12. The process of claim 3 wherein the light feed is ethane.

13. The process of claim 11 wherein the light feed is ethane.

14. The process of claim 10 wherein the dilution gas is superheated steam.

* * * * *